United States Patent
Belyakov et al.

(10) Patent No.: US 7,244,288 B2
(45) Date of Patent: Jul. 17, 2007

(54) PULSED VAPOR DESORBER

(75) Inventors: Vladimir V. Belyakov, Lynn, MA (US); Daniel E. Jonsen, Beverly, MA (US); Stephen N. Bunker, Wakefield, MA (US)

(73) Assignee: Implant Sciences Corporation, Wakefield, MA (US)

( * ) Notice: Subject to any disclaimer, the term of this patent is extended or adjusted under 35 U.S.C. 154(b) by 320 days.

(21) Appl. No.: 10/853,563

(22) Filed: May 25, 2004

(65) Prior Publication Data

US 2004/0248319 A1 Dec. 9, 2004

Related U.S. Application Data

(60) Provisional application No. 60/473,649, filed on May 28, 2003.

(51) Int. Cl.
*B01D 53/02* (2006.01)
(52) U.S. Cl. .............................. 95/90; 95/148
(58) Field of Classification Search ............... 95/90, 95/106, 114, 115, 148; 96/108, 143, 146, 96/154, 413; 73/23.2, 863, 863.11, 863.12, 73/863.71
See application file for complete search history.

(56) References Cited

U.S. PATENT DOCUMENTS

| | | | | |
|---|---|---|---|---|
| 4,910,965 A | * | 3/1990 | Lepofsky et al. | 62/55.5 |
| 5,482,524 A | * | 1/1996 | Nakano et al. | 422/285 |
| 5,667,559 A | * | 9/1997 | Vickery | 95/110 |
| 6,149,717 A | * | 11/2000 | Satyapal et al. | 96/16 |
| 6,517,610 B1 | * | 2/2003 | de la Houssaye | 95/107 |
| 6,605,814 B1 | * | 8/2003 | Tadika et al. | 250/492.2 |

OTHER PUBLICATIONS

U.S. Appl. No. 10/295,010 filed Nov. 14, 2002, Cyclone Sampling Nozzle for an Ion Mobility Spectrometer, Motchkine et al.
U.S. Appl. No. 10/295,039 filed Nov. 14, 2002, Radiative Sample Warming for an Ion Mobility Spectrometer, Motchkine et al.
U.S. Appl. No. 10/349,491 filed Jan. 22, 2003, Explosive Detection System, Krasnobaev et al.
U.S. Appl. No. 10/754,088 filed Jan. 7, 2004, Virtual Wall Gas Sampling for an Ion Mobility Spectrometer, Krasnobaev et al.
U.S. Appl. No. 10/818,434 filed Apr. 5, 2004, Modified Vortex for an Ion Mobility Spectrometer, Krasnobaev et al.
U.S. Appl. No. 10/890,820 filed Jul. 14, 2004, Flash Vapor Sampling for a Trace Chemical Detector, Belyakov et al.

* cited by examiner

*Primary Examiner*—Frank M. Lawrence
(74) *Attorney, Agent, or Firm*—Muirhead & Saturnelli, LLC

(57) ABSTRACT

Vapor concentrators are used to provide a higher concentration of trace target vapor than would normally be available in the environment. This is accomplished by allowing the trace target vapor to adsorb onto a concentrating surface and subsequently releasing the trace target vapor by heating the surface. An improved desorbing method is providing by a fast pulse of photons, which only heats the near surface region, rather than the entire mass of the substrate on which the concentrating surface resides. Since all of the trace target vapor is released in a short time interval, the vapor is less diluted by carrier gas than would occur during the slower temperature ramp that results when the entire substrate mass is heated. A more highly concentrated target vapor is produced with less input of energy.

7 Claims, 3 Drawing Sheets

PULSED VAPOR DESORBER

CROSS-REFERENCE TO RELATED APPLICATIONS

This application claims priority to U.S. Provisional Application No. 60/473,649, filed May 28, 2003, which is incorporated herein by reference.

BACKGROUND OF THE INVENTION

1. Field of the Invention

This invention relates to a vapor concentrator that may interface to an instrument that detects trace quantities of chemicals present as vapors in air or other gases, or liberated as vapors from condensed phases, such as particles or solutions, and more particularly relates to the desorption of concentrated samples of such vapors for injection into analytical instruments.

2. Description of Related Art

The quantitative analysis and identification of trace organic vapor species is rapidly becoming important in a variety of applications. For example, trace vapors are used to indicate the presence or recent handling of various explosive compounds. Detection of toxic chemicals, narcotic substances, fumes from food decay, fumes from printer's inks used in the manufacture of money, medically significant compounds released by bacteria, and industrial processing chemical indicators are just some of the applications currently utilizing the analysis of trace chemical vapors. Often, the volume concentrations of these vapors in air will be in the range of parts per million (ppm) to parts per trillion (ppt) or even less.

A variety of highly sensitive gas analysis measurement techniques already exist for recognizing vapors in this concentration range, which include, but are not limited to, ion mobility spectroscopy (IMS), gas chromatography (GC), flash gas chromatography (fast GC), and mass spectroscopy (MS). The sensitivity of these well-known techniques is often limited by the low concentration of the target chemical vapors that are present at their input ports.

The volume concentration of vapor entering the input port of the analysis device can be increased compared to the ambient concentration using a device called a vapor concentrator or vapor preconcentrator. A variety of concentration designs have been described. See, for example, U.S. Pat. No. 4,987,767, which describes a rotating metal screen and heater device. Explosives vapors are adsorbed onto the metal screen in the concentration phase and subsequently desorbed by a heating phase at a different rotational position. See also U.S. Pat. No. 6,085,601, which describes an adsorbing filter screen substantially perpendicular to the air flow for use in the concentration phase, and resistively heating said screen in the desorbing phase. See also U.S. Pat. No. 6,239,428, which describes a concentrator consisting of either a permeable organic membrane or a thin metal foil that is heated for the desorbing phase. See also U.S. Pat. No. 5,585,375, which is similar to U.S. Pat. No. 4,987,767 but with a concentration-enhancing coating on the rotating metal screen, and U.S. Pat. No. 6,345,545, which is similar to U.S. Pat. No. 6,085,601 but with a multistage filter screen method.

All of these vapor concentration devices utilize the tendency of vapors to adsorb onto a surface. The surface may optionally be selectively coated with an adsorption-enhancing chemical. The adsorbing surface is subsequently heated to desorb the accumulated vapor, either by means of an included heating element or by means of an external oven. If the heating is external, thermal communication is by hot air, substantially continuous electromagnetic radiation, a heat pipe, or a mixture of these methods. An included heating element may be an electrically resistive heater, but may also be a semiconductor device using the Peltier effect. The resistive heater may be pulsed, and the temperature versus time profile may be controlled, to cause more volatile compounds to be preferentially desorbed at an earlier time in the cycle. High temperature surface cleaning steps may also be included in the total cycle of operation. Further improvements include multiple stages of independent concentration surfaces that may be sequentially heated to bunch the vapor into a short duration pulse or alternatively may be sequentially heated at different temperatures to induce separation of chemicals by volatility.

The vapor drawn from the concentration device may be a mixture of a carrier gas, such as ambient air, nitrogen, or an inert gas, the target molecule or molecules, and other possibly interfering chemicals. Separation, combined with identification of the target compound, is performed by the analytical instrument. The analytical instrument's sampling method may employ a gas pump, which draws the sample gas from the concentrator into the instrument through a tube. For example, the pump may be disposed to provide a partial vacuum at the exit of an ion source, which is a component of the analytical instrument. This partial vacuum may be transmitted through the confines of the ion source and appear at the entrance orifice of the ion source. A further tubulation may be provided as an extension to a more conveniently disposed sampling orifice external to the analytical instrument. Molecules of interest may undesirably adsorb onto surfaces in the sampling flow path that are not part of the concentration device. Therefore, heating of the connecting tubulation may be required to minimize loss of vapor.

All of these concentration methods are limited by the fact that the relatively large mass of the substrate must change temperature, a relatively slow process. The rate of temperature rise relates to the power used to heat the substrate of the adsorbing surface divided by the mass being heated divided by the heat capacity of the substrate. Thus, a low mass, as well as a low heat capacity, allows the adsorbing surface to be heated at a faster rate. This is particularly useful for portable devices where high power is not usually available from batteries.

The volume concentration of the concentrated vapors as presented to the analytical instrument depends on the release rate of target vapor off of the adsorbing surface relative to the flow rate of the carrier gas. If all of the adsorbed target vapor could be released more rapidly, the volume concentration of target vapor presented to the analytical instrument may be substantially increased, and the signal-to-noise ratio and sensitivity may be greatly improved.

SUMMARY OF THE INVENTION

According to the present invention, a method for the rapid desorption of adsorbed gases in a vapor concentrator system is described. This method includes providing a substrate with a surface for adsorbing target vapor, accumulating target vapor on the substrate surface, providing a short duration pulse of photons from a lamp onto the substrate surface to desorb the target vapor, and providing a carrier gas flow for transporting the desorbed target vapor to an analytical instrument for detecting the target vapor.

According further to the present invention, the substrate may be a plurality of surfaces and may be enclosed in a chamber with at least one entrance orifice and at least one exit orifice for the passage of the carrier gas and the target vapor. The carrier gas may be at least one of air, nitrogen, an inert gas, carbon dioxide, hydrogen, ammonia, and water vapor. The inert gases may be helium, neon, krypton, and xenon. The surface of the substrate may be coated with an adsorption-enhancing chemical. Depending on the nature of the target vapor, a large number of such chemicals are known. Exemplary coatings include polydimethylsiloxane, which may be crosslinked with divinylbenzene. Additional coatings are available from Supelco, a Sigma-Aldrich company.

According further to the present invention, portions or all of the chamber and orifices may be independently heated to minimize adsorption onto their respective surfaces.

According further to the present invention, the pulse of photons that induce desorption of the target vapor should be less than 100 milliseconds and should comprise wavelengths between the infrared and ultraviolet. The lamp that produces the pulse of photons may contain an inert gas, such as xenon, krypton, neon, or a mixture of inert gases. The energy for the pulse of photons may be provided by the discharge of a high voltage capacitor through an electronic circuit.

According further to the present invention, the pulse of photons may be in optical communication with the entirety of the surface for adsorbing target vapor without significant shadowing of portions of the surface. Full optical communication maximizes vapor desorption and allows vapor accumulated during a concentration cycle to be completely cleared before a subsequent cycle. The optical communication may optionally include an optically transparent window, an optically transparent lens, a mirror for concentration and containment of the pulse of photons, a light pipe, or an optical fiber. The optically transparent window may optionally be a component of the lamp.

The concentration phase may include passing sample gas containing trace target vapor and a carrier gas through the entrance orifice and over the adsorbing surface of the substrate within the chamber. The desorption phase may include providing a pulse of photons onto the adsorbing surface to desorb the accumulated target vapor. A carrier gas may entrain the desorbed vapor and pass through the exit orifice of the chamber. The pulse of vapor may be transported with the carrier gas to an analytical instrument for determination of the presence of the target vapor. A separate oven or heater for completely removing any residual adsorbed vapor remaining after the photon pulse may optionally be provided, with the released vapor produced by the oven or heater directed not to the analytical instrument but outside the chamber.

In one embodiment, a high brightness pulsed lamp, such as a xenon-filled lamp, is used to illuminate the adsorbing surface for a time period less than 100 milliseconds, for example, less than 1 millisecond. Additionally, the geometry of the adsorbing surface may be totally illuminated without any significant shadowing. The energy transmitted by the pulse of photons from the lamp may be much smaller than that required to heat the entire substrate of the adsorbing surface to a given temperature. Still, the surface layer of the adsorbing surface, which only includes a few hundred monolayers of atoms, may not conduct this sudden influx of energy away instantaneously, and thus the adsorbing surface may momentarily become relatively warm. The effect may last only for a few milliseconds before thermal conduction dissipates the energy into the substrate of the adsorbing material, and the surface layers cool off.

The advantages of this method are as follows: 1) relatively little energy is needed to warm only the surface layer of the adsorber, which is useful in field portable implementations, 2) the adsorbing surface is purged and ready to be reused immediately, that is, no time is needed for cool down, and 3) all of the target vapors are released into the carrier gas stream relatively quickly (e.g., within about 1 millisecond), providing a much higher concentration of target vapor than can be obtained by thermally heating the entire adsorbing mass, which may require seconds to accomplish.

In one embodiment, the adsorbing surface is a flat surface, such as a foil or disk, or the outside or inside of a curved surface, such as a cylinder. Such surfaces lack significant shadowed areas that may accumulate vapors but release them slowly subsequent to a photon pulse. These incompletely desorbed vapors may lead to false positive signals subsequent to a true positive event. The extent of shadowing depends on the exact geometry employed but increases when substrates with irregular three dimensional surfaces, such as porous materials, are used. Shadowing may be increased when geometrics such as a pervious woven wire mesh screen, a pervious metallic felt, and the inside of capillary tubes are used.

In one embodiment, the concentration method avoids the accumulation of particles, as compared to the desired vapors. Particles may be relatively massive, and the pulsed lamp may not produce sufficient photonic energy to completely vaporize them. Incompletely vaporized particles may continue to emit vapor during later cycles of adsorption/desorption, causing false positive indications in the analysis instrument. Particles can be excluded from the interior of the chamber by, for example, limiting flow rates to reduce turbulence, using a cyclone dust separator, or using a filter.

A method of concentrating vapors uses a specially coated fiber as the adsorbing surface, a technique known as solid phase micro extraction (SPME). SPME fibers are sold for use with GC systems, and there exists a wide selection of fiber materials and adsorption enhancing coatings, which allow increased specificity for certain classes of target chemical vapors. The inclusion of such SPME fibers in a vapor concentrator is one embodiment of this application.

BRIEF DESCRIPTION OF THE DRAWING

The invention is described with reference to the several figures of the drawing, in which.

DETAILED DESCRIPTION

Figure 1:
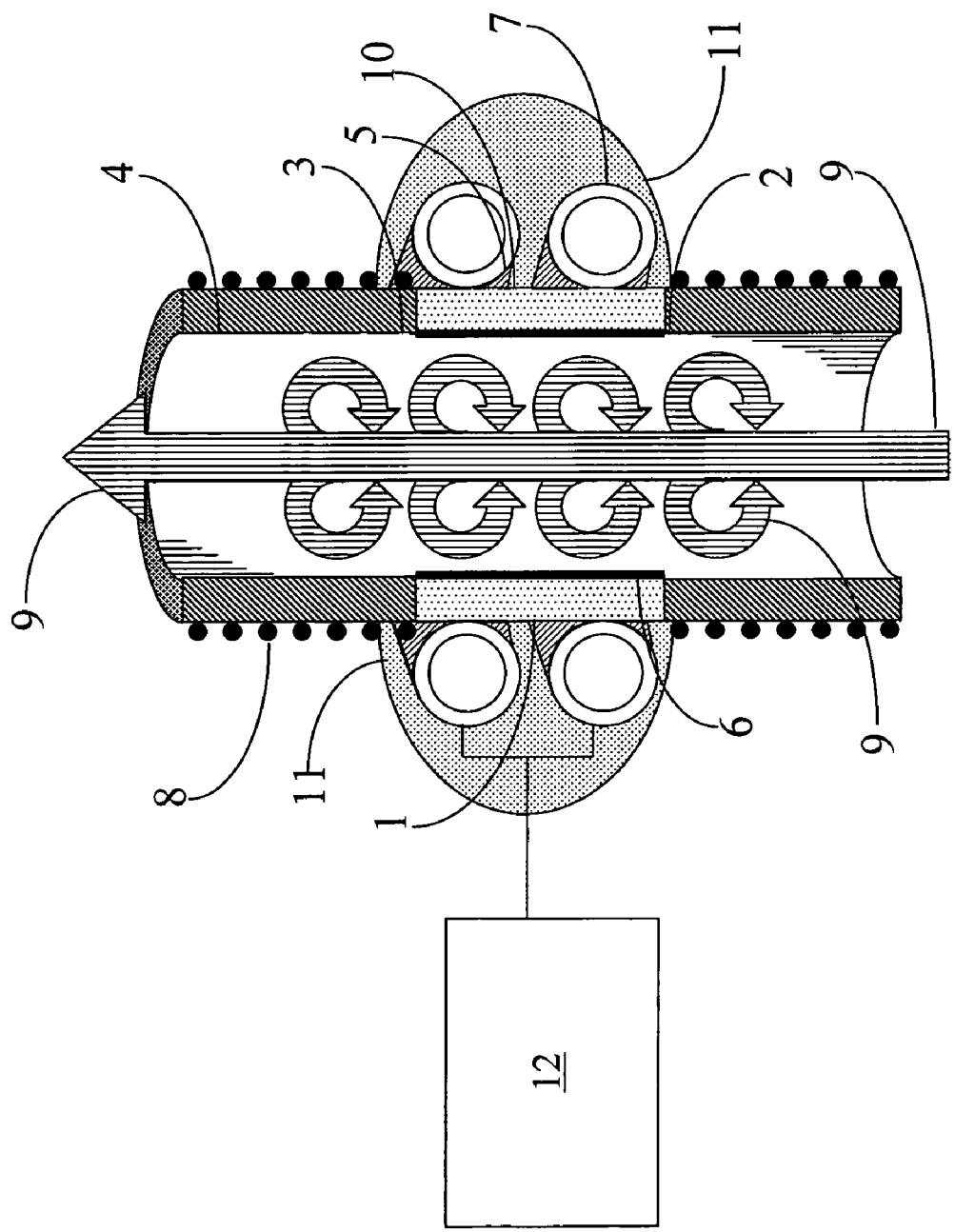
FIG. 1 is a schematic diagram showing an exemplary embodiment of a pulsed desorption concentrator system using a cylindrical concentrating surface with the chamber, optical communication window, and substrate as all the same component.

A possible embodiment of a pulsed desorption vapor concentrator is illustrated in FIG. 1. While various embodiments may differ in details, FIG. 1 shows many of the basic features of a type of concentrator that could be used in connection with the pulsed vapor desorption method described herein. The concentrator includes a chamber 1, which in this embodiment is also an optical communication window 10 connecting a pulsed lamp 7 to a substrate 5 of a concentrating surface 6. In this embodiment, the substrate 5 is also the same as the chamber 1 and the optical communication window 10. A mixture of carrier gas and trace target vapor 9 enters the chamber 1 through an entrance orifice 2. Due to turbulence, the flow interacts with the concentrating surface 6. The concentrating surface 6 may be the wall of the optical communication window 10 or it may optionally be a thin, semitransparent coating on the optical communication window 10. A heater 8 is used to warm any tubulation that may be attached to an entrance 2 of the chamber 1 as well as tubulation 4 that may be attached to an exit orifice 3 of the chamber 1. The tubulation 4 is in communication with an analytical instrument (not shown) that analyzes the concentrated vapor that is released from the concentrating surface 6 when the lamp 7 is pulsed. The lamp 7 may be one or may be a plurality of lamps. The lamp 7 may be a straight tube, a torus-shaped tube, or a spiral-shaped tube. In one embodiment, the lamp 7 contains an inert gas, such as xenon. An electric circuit 12 connected to the lamp 7 contains a high voltage capacitor that is abruptly discharged through the lamp 7 to provide the energy to produce an intense pulse of photons. An optional reflector 11 may be used to contain and concentrate the flux of photons. In one embodiment, the photons have wavelengths in the range between infrared and ultraviolet.

Figure 2:
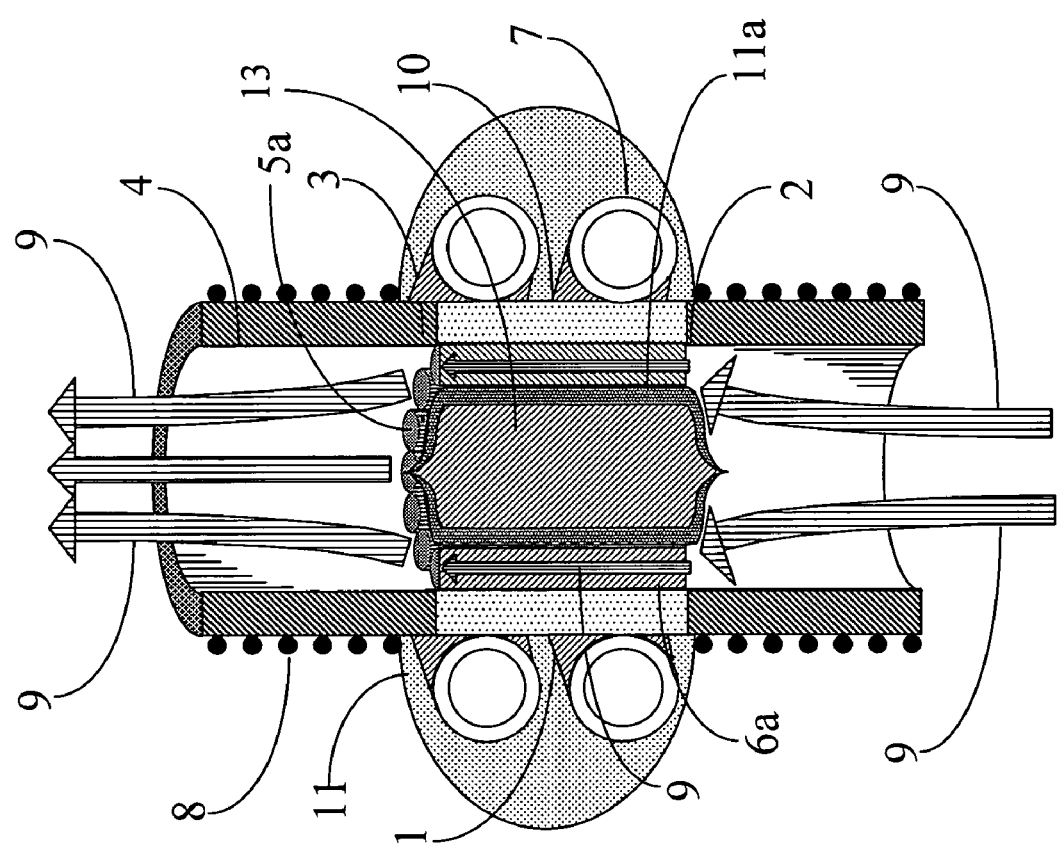
FIG. 2 is a schematic diagram showing an exemplary embodiment of a pulsed desorption concentrator system using a cylindrical concentrating surface with the chamber and optical communication window as the same component and with a separate substrate comprising SPME fibers.

FIG. 2 shows a second embodiment of a pulsed desorption vapor concentrator. This embodiment resembles that of FIG. 1 except that a separate plurality of substrates 5a with concentrating surfaces 6a have been provided. The substrates 5a may be SPME fibers. A chamber 1 contains the plurality of substrates 5a with optical communication to the pulsed lamp 7 through the optical window 10, which is the same element as the chamber 1. A mixture of carrier gas and trace target vapor 9 is introduced through the entrance orifice 2 of chamber 1. The heater 8 is used to heat the walls before the entrance orifice 2 and after the exit orifice 3 of chamber 1 in order to minimize adsorption on these surfaces. The vapor is accumulated on the plurality of concentrating surfaces 6a until it is desorbed by the photons produced by the pulsing lamp 7. The desorbed vapor and carrier gas proceeds out the exit orifice 3 and through the tubulation 4 into the analytical instrument (not shown) that analyzes the vapor. In the embodiment depicted in FIG. 2, a reflector 11 is used to concentrate and contain the photons from the lamp 7. One or more reflectors may optionally be employed. In one embodiment, the reflector forms a shell around the lamp 7 to direct light back into the chamber 1. A central tube 13 may be disposed in the interior of chamber 1 and may optionally have an additional reflecting surface 11a for photon concentration and containment. Alternatively, the central tube 13 may optionally include one or more lamps for additional photon generation and to avoid shadowing. Optionally, the central tube 13 may have an concentration surface and be another substrate. In all cases the concentrating surface may be the surface of the substrate or an adsorption enhancing coating on the substrate.

Figure 3:
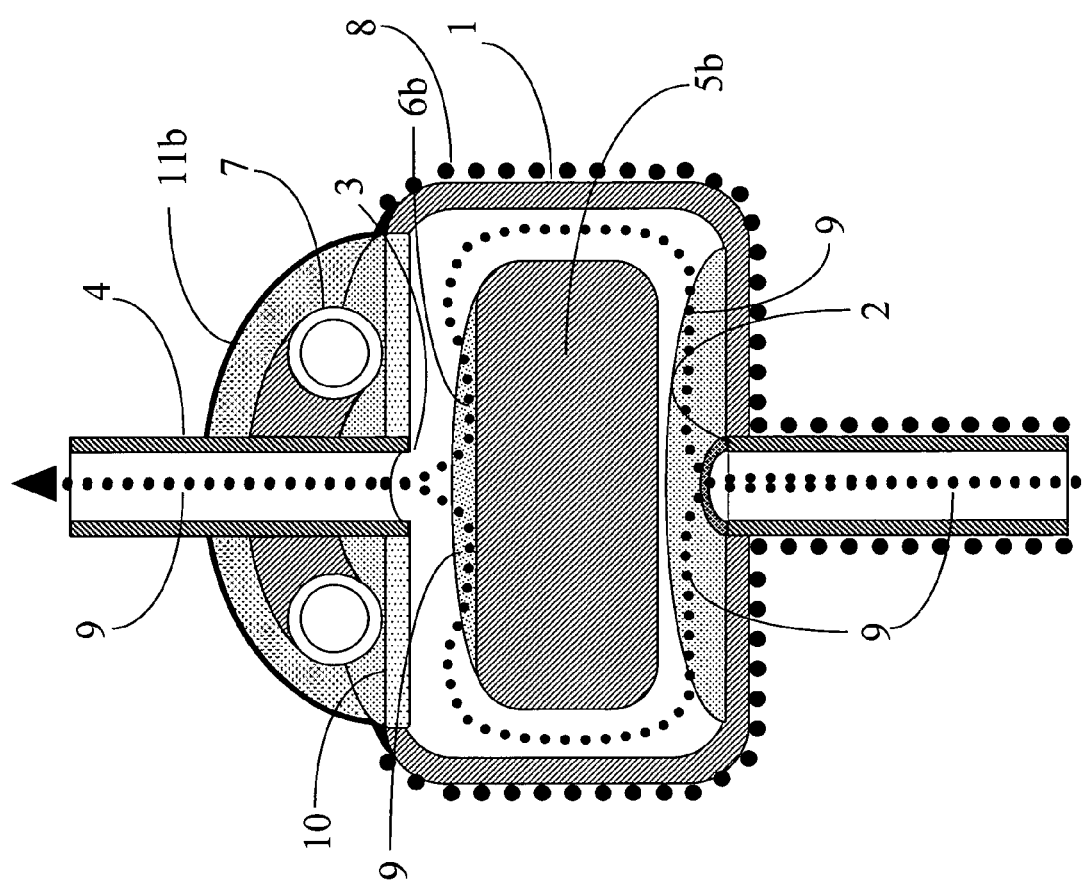
FIG. 3 is a schematic diagram showing an exemplary embodiment of a pulsed desorption concentrator system using a planar concentrating surface with the optical communication window as a portion of the chamber and with a separate substrate.

A third alternate embodiment for a pulsed desorption vapor concentrator is shown in FIG. 3. The concentrating surface 6b of substrate 5b is planar, rather than cylindrical. A chamber 1 surrounds substrate 5b, and the walls of chamber 1 are heated by heater 8 in order to minimize adsorption of target vapor on its surface. The mixture of carrier gas and trace target vapor 9 enters chamber 1 through entrance orifice 2, which is heated by heater 8. A portion of chamber 1 contains a window 10 for optical communication between the concentrating surface 6b and the pulsed lamp 7. A reflector 11b is used for concentrating and containing the photon flux from pulsed lamp 7. When the lamp 7 is pulsed, the accumulated target vapor is desorbed and entrained in the carrier gas flow 9. The flow 9 leaves chamber 1 through exit orifice 3 and into tubulation 4, which connects to the analytical instrument (not shown) for analysis of the target vapor. The concentrating surface may be the surface of substrate 5 or optionally an adsorption enhancing coating on substrate 5b.

The three basic geometries of FIGS. 1–3 are in no way intended to limit the types of geometries of vapor concentration devices that may be employed with pulsed desorption of vapor. For example, the substrate may be mechanically moved from one chamber to one or more other chambers in order to isolate the gas flow of unconcentrated trace target vapor from a separate region that is in direct communication with the analytical instrument. This method controls the quantity and type of vapor capable of reaching the analytical instrument. Alternately, a plurality of gas valves may optionally be employed to open or close the operational entrance orifice and exit orifice at different times in the concentrating/desorption/surface-cleaning cycle. This method can be utilized to optimally adjust the rate of flow for carrier gas and trace target vapor between the concentrating mode and the desorption mode.

What is claimed is:

1. A method for the rapid desorption of adsorbed gases in a vapor concentrator system comprising:

providing a chamber with at least one entrance orifice and at least one exit orifice for the passage of vapor;

providing a carrier gas moved by a gas pump to assist the passage of trace target vapor into and out of said chamber;

providing at least one substrate with a surface for the concentration of said trace target vapor within said chamber;

providing at least one lamp that emits photons in optical communication with said surface of said substrate;

providing an electronic circuit that energizes said lamp, wherein the lamp is induced to produce a main pulse of photons with a duration less than 100 milliseconds;

passing gas containing said trace target vapor over said substrate to accumulate said target vapor through adsorption on said surface;

emitting said main pulse of photons to induce said trace target vapor to rapidly desorb from said surface of said substrate; and passing said carrier gas over said substrate to assist said desorbed trace target vapor in being swept from said chamber through said exit orifice.

2. A method for rapid desorption as in claim 1 wherein said carrier gas is at least one of air, nitrogen, an inert gas, carbon dioxide, hydrogen, ammonia, and water vapor.

3. A method for rapid desorption as in claim 1 wherein the surface of said substrate is coated with an adsorption-enhancing chemical.

4. A method for rapid desorption as in claim 1 wherein said lamp contains an inert gas.

5. A method for rapid desorption as in claim 1 wherein said main pulse of photons includes wavelengths in at least one of infrared, visible, and ultraviolet.

6. A method for rapid desorption as in claim 1 wherein said chamber includes at least one component that is heated to reduce adsorption of said trace target vapor on the surface of said component.

7. A method for rapid desorption as in claim 1 wherein said lamp is in optical communication with at least one optically reflecting surface to concentrate and contain a photon flux from the main pulse.

* * * * *